US011197950B2

(12) United States Patent
Shalaby

(10) Patent No.: US 11,197,950 B2
(45) Date of Patent: *Dec. 14, 2021

(54) ABSORBABLE PERMEABILITY-MODULATED BARRIER COMPOSITES AND APPLICATIONS THEREOF

(71) Applicant: Poly-Med, Inc., Anderson, SC (US)

(72) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/931,552

(22) Filed: Jul. 17, 2020

(65) Prior Publication Data

US 2020/0345900 A1 Nov. 5, 2020

Related U.S. Application Data

(63) Continuation of application No. 16/014,184, filed on Jun. 21, 2018, now Pat. No. 10,751,449, which is a continuation of application No. 15/350,067, filed on Nov. 13, 2016, now Pat. No. 10,004,833, which is a continuation of application No. 12/284,657, filed on Sep. 24, 2008, now Pat. No. 9,492,593.

(51) Int. Cl.
| | |
|---|---|
| *A61L 31/12* | (2006.01) |
| *A61F 2/00* | (2006.01) |
| *A61L 27/48* | (2006.01) |
| *A61L 31/14* | (2006.01) |
| *D01D 5/00* | (2006.01) |
| *A61L 27/58* | (2006.01) |
| *A61B 17/42* | (2006.01) |
| *A61B 90/00* | (2016.01) |

(52) U.S. Cl.
CPC .......... *A61L 31/129* (2013.01); *A61F 2/0063* (2013.01); *A61L 27/48* (2013.01); *A61L 27/58* (2013.01); *A61L 31/148* (2013.01); *D01D 5/003* (2013.01); *A61B 17/42* (2013.01); *A61B 2090/0816* (2016.02); *A61L 2430/22* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,284,506 A | 8/1981 | Tetenbaum et al. | |
| 5,508,036 A | 4/1996 | Bakker et al. | |
| 5,714,159 A | 2/1998 | Shalaby | |
| 5,795,584 A | 8/1998 | Totakura et al. | |
| 6,197,036 B1 | 3/2001 | Tripp et al. | |
| 6,319,264 B1* | 11/2001 | Tormala ................ | A61F 2/0063 606/151 |
| 6,462,169 B1 | 10/2002 | Shalaby | |
| 6,576,019 B1 | 6/2003 | Atala | |
| 6,599,323 B2 | 7/2003 | Melican et al. | |
| 6,884,428 B2 | 4/2005 | Binette et al. | |
| 6,936,052 B2 | 8/2005 | Gellman et al. | |
| 7,041,713 B2 | 5/2006 | Yamauchi et al. | |
| 7,172,765 B2 | 2/2007 | Chu et al. | |
| 7,371,256 B2 | 5/2008 | Shalaby | |
| 7,390,452 B2 | 6/2008 | Balkus, Jr. et al. | |
| 8,048,448 B2 | 11/2011 | Ludwig et al. | |
| 8,585,772 B2 | 11/2013 | Shalaby et al. | |
| 9,492,593 B2 | 11/2016 | Shalaby | |
| 2002/0161168 A1* | 10/2002 | Shalaby ................. | C08G 63/64 528/310 |
| 2004/0265355 A1 | 12/2004 | Shalaby | |
| 2005/0260706 A1 | 11/2005 | Kaplan et al. | |
| 2006/0013863 A1 | 1/2006 | Shalaby et al. | |
| 2006/0085063 A1 | 4/2006 | Shastri et al. | |
| 2007/0292495 A1 | 12/2007 | Ludwig et al. | |
| 2008/0119848 A1 | 5/2008 | Shalaby et al. | |
| 2008/0184453 A1 | 8/2008 | Conley et al. | |
| 2008/0208323 A1 | 8/2008 | El-Kurdi et al. | |

FOREIGN PATENT DOCUMENTS

| | | |
|---|---|---|
| WO | 1998014134 | 4/1998 |
| WO | 2005079335 | 9/2005 |
| WO | 2008100842 | 8/2008 |

OTHER PUBLICATIONS

U.S. Appl. No. 12/248,657 (U.S. Pat. No. 9,492,593), filed Sep. 20, 2008 (Nov. 15, 2016), Shalaby.
U.S. Appl. No. 15/350,067, (U.S. Pat. No. 10,004,833), filed Nov. 13, 2016 (Jun. 26, 2018), Shalaby.
U.S. Appl. No. 16/014,184 (U.S. Pat. No. 10,751,449), filed Jun. 21, 2018, (Aug. 25, 202), Shalaby.
Nonfinal Office Action, dated Apr. 15, 2010, for U.S. Appl. No. 12/284,657, filed Sep. 24, 2008, now U.S. Pat. No. 9,492,593, inventor: S. Shalaby, 14 pgs.
Response to NonFinal Office Action, dated Jul. 14, 2010, for U.S. Appl. No. 12/284,657, filed Sep. 24, 2008, now U.S. Pat. No. 9,492,593, inventor: S. Shalaby, 11 pgs.
Final Office Action, dated Sep. 24, 2010, for U.S. Appl. No. 12/284,657, filed Sep. 24, 2008, now U.S. Pat. No. 9,492,593, inventor: S. Shalaby, 14 pgs.
Response to Final Office Action, dated Mar. 24, 2011, for U.S. Appl. No. 12/284,657, filed Sep. 24, 2008, now U.S. Pat. No. 9,492,593, inventor: S. Shalaby, 14 pgs.
NonFinal Office Action, dated Feb. 17, 2014, for U.S. Appl. No. 12/284,657, filed Sep. 24, 2008, now U.S. Pat. No. 9,492,593, inventor: S. Shalaby, 20 pgs.

(Continued)

*Primary Examiner* — Susan T Tran
*Assistant Examiner* — William Craigo

(57) ABSTRACT

Absorbable barrier composites are designed for modulated gas and water permeability depending on clinical use and are formed of at least two physicochemically distinct components, one of which is a film adjoined to a knitted mesh and/or electrostatically spun, non-woven fabric. Depending on the physicochemical properties of the barrier composite, it can be used in neurological and urinogenital surgical procedures as well as tissue engineering and/or as physical barriers to prevent adhesion formation following several types of surgical procedures.

34 Claims, No Drawings

(56) References Cited

OTHER PUBLICATIONS

Response to NonFinal Office Action, dated Jun. 6, 2014, for U.S. Appl. No. 12/284,657, filed Sep. 24, 2008, now U.S. Pat. No. 9,492,593, inventor: S. Shalaby, 16 pgs.
Applicant/Examiner Interview, dated Jun. 13, 2014, for U.S. Appl. No. 12/284,657, filed Sep. 24, 2008, now U.S. Pat. No. 9,492,593, inventor: S. Shalaby, 3 pgs.
Response to NonFinal Office Action, dated Dec. 4, 2014, for U.S. Appl. No. 12/284,657, filed Sep. 24, 2008, now U.S. Pat. No. 9,492,593, inventor: S. Shalaby, 16 pgs.
Final Office Action, dated Mar. 14, 2015, for U.S. Appl. No. 12/284,657, filed Sep. 24, 2008, now U.S. Pat. No. 9,492,593, inventor: S. Shalaby, 19 pgs.
Response to Final Office Action, dated Jun. 12, 2015, for U.S. Appl. No. 12/284,657, filed Sep. 24, 2008, now U.S. Pat. No. 9,492,593, inventor: S. Shalaby, 13 pgs.
Advisory Action, dated Jul. 2, 2015, for U.S. Appl. No. 12/284,657, filed Sep. 24, 2008, now U.S. Pat. No. 9,492,593, inventor: S. Shalaby, 5 pgs.
NonFinal Office Action, dated Feb. 12, 2016, for U.S. Appl. No. 12/284,657, filed Sep. 24, 2008, now U.S. Pat. No. 9,492,593, inventor: S. Shalaby, 16 pgs.
Response to NonFinal Office Action, dated May 6, 2016, for U.S. Appl. No. 12/284,657, filed Sep. 24, 2008, now U.S. Pat. No. 9,492,593, inventor: S. Shalaby, 13 pgs.
Notice of Allowance, dated Jul. 15, 2016, for U.S. Appl. No. 12/284,657, filed Sep. 24, 2008, now U.S. Pat. No. 9,492,593, inventor: S. Shalaby, 9 pgs.
NonFinal Office Action, dated Sep. 13, 2017, for U.S. Appl. No. 115/350,067, filed Nov. 13, 2016, now U.S. Pat. No. 10,004,833, inventor: S. Shalaby, 7 pgs.
Response to NonFinal Office Action, dated Jan. 16, 2018, for U.S. Appl. No. 115/350,067, filed Nov. 13, 2016, now U.S. Pat. No. 10,004,833, inventor: S. Shalaby, 8 pgs.
Notice of Allowance, dated Feb. 28, 2018, for U.S. Appl. No. 115/350,067, filed Nov. 13, 2016, now U.S. Pat. No. 10,004,833, inventor: S. Shalaby, 7 pgs.
Preliminary Amendment, filed Oct. 24, 2018, for U.S. Appl. No. 16/014,184, filed Jun. 21, 2018, 6 p.
Restriction Requirement, dated Jun. 25, 2019, for U.S. Appl. No. 16/014,184, filed Jun. 21, 2018, 11 p.
Response to Restriction Requirement, dated Aug. 26, 2019, for U.S. Appl. No. 16/014,184, filed Jun. 21, 2018, 5 p.
NonFinal Office Action, dated Nov. 18, 2019, for U.S. Appl. No. 16/014,184, filed Jun. 21, 2018, 10 p.
Response to NonFinal Office Action, dated Mar. 18, 2020, for U.S. Appl. No. 16/014,184, filed Jun. 21, 2018, 9 p.
Notice of Allowance, dated Apr. 15, 2020, for U.S. Appl. No. 16/014,184, filed Jun. 21, 2018, 9 p.
2nd Notice of Allowance, dated Jun. 24, 2020, for U.S. Appl. No. 16/014,184, filed Jun. 21, 2018, 5 p.
Issue Notification, dated Aug. 5, 2020, for U.S. Appl. No. 16/014,184, filed Jun. 21, 2018, 1 p.

\* cited by examiner

ABSORBABLE PERMEABILITY-MODULATED BARRIER COMPOSITES AND APPLICATIONS THEREOF

CROSS-REFERENCE TO RELATED APPLICATION

This application is a continuation of U.S. patent application Ser. No. 16/014,184, filed Jun. 21, 2018, now U.S. Pat. No. 10,751,449, which is a continuation of U.S. patent application Ser. No. 15/350,067, filed Nov. 13, 2016, now U.S. Pat. No. 10,004,833, which is a continuation of U.S. patent application Ser. No. 12/284,657, filed Sep. 24, 2008, which is now U.S. Pat. No. 9,492,593, each of which is herein incorporated in its entirety.

FIELD OF THE INVENTION

This invention is directed to absorbable barrier composites with modulated gas and water permeability, the composite formed of a flexible film and at least one fibrous or microfibrous adjoining component in the form of knitted mesh or electrospun, non-woven fabric, respectively. These composites can be tailored to allow their use in neurological and urinogenital procedures and particularly those associated with spine, cranial and urinary bladder prostheses. Due to their flexibility and barrier properties, these composites are suitable for use in the prevention of adhesion formation following several types of surgical procedures.

BACKGROUND

The use of sutures and meshes made from absorbable polymers has been disclosed in numerous patents for the past four decades. However, over the past three decades, the use of absorbable fibers in fibrous composites has been limited for the most part to bicomponent composites for use in (1) solid fiber-reinforced orthopedic devices, and to a lesser extent, (2) synthetic absorbable vascular grafts. Availability of new types of fiber-forming and microfiber-forming absorbable polymers led to the development, in this laboratory, of a number of fibrous and microfibrous medical constructs having a broad range of properties. These include (1) fully or partially absorbable composites for urological and vascular applications [U.S. Pat. No. 7,371,256 (2002); U.S. patent application Ser. No. 10/860,677 (2003); U.S. patent application Ser. No. 11/175,635 (2005); U.S. patent application Ser. No. 11/204,822 (2005); and U.S. patent application Ser. No. 11/346,117 (2006)], and fully or selectively absorbable knitted meshes [U.S. patent application Ser. No. 11/886,370 (2007); U.S. patent application Ser. No. 11/978,795 (2007); U.S. patent application Ser. No. 11/983,321 (2007)]. However, none of these composites was claimed as having permeability-modulated barrier properties to allow their application as medical devices or components thereof for use in conjunction with the surgical procedures noted in the present invention. Most important among such procedures are those dealing with prosthetic dura mater and patches for repairing the urinary bladder and vascular tissue and/or their tissue engineering. Accounts of the prior art related to the area are described below.

In a disclosure on bladder reconstruction that is pertinent to the instant invention (U.S. Pat. No. 6,576,019) the inventor provided a useful background to his invention, excerpts of which are summarized below:

The human urinary bladder is a musculomembranous sac situated in the anterior part of the pelvic cavity and serves as a reservoir for urine, which it receives through the ureters and discharges through the urethra. The bladder ureters and urethra are all similarly structured in that they comprise muscular structures lined with a membrane comprising urothelial cells coated with mucus that is impermeable to the normal soluble substances of the urine. The bladder tissue is elastic and compliant. That is, the bladder changes shape and size according to the amount of urine it contains. A bladder resembles a deflated balloon when empty but becomes somewhat pear-shaped and rises in the abdominal cavity when the amount of urine increases.

The bladder wall has three main layers of tissues: the mucosa, submucosa, and detrusor. The mucosa, comprising urothelial cells, is the innermost layer. The submucosa lies immediately beneath the mucosa and its basement membrane. It is composed of blood vessels which supply the mucosa with nutrients and the lymph nodes which aid in the removal of waste products. The detrusor is a layer of smooth muscle cells which expands to store urine and contracts to expel urine. The bladder is subjected to numerous maladies and injuries which cause deterioration which may result from infectious diseases, neoplasms and developmental abnormalities. Further, bladder deterioration may also occur as a result of trauma such as, for example, car accidents and sports injury.

Although a large number of biomaterials, including synthetic and naturally derived polymers, have been employed for tissue reconstruction or augmentation, no material has proven satisfactory for use in bladder reconstruction. For example, synthetic biomaterials such as polyvinyl and gelatin sponges, polytetrafluoroethylene, and silastic patches have been relatively unsuccessful, generally due to foreign body reactions. Other attempts have usually failed due to mechanical, structural, functional, or biocompatibility problems. Permanent synthetic materials have been associated with mechanical failure and calculus formation. Naturally derived materials such as lyophilized dura, deepithelialized bowel segments, and small intestinal submucosa have also been proposed for bladder replacement. However, it has been reported that bladders augmented with dura, peritoneum placenta, and fascia contract over time.

In an effort to circumvent the drawbacks of the prior art disclosed in, Atala, U.S. Pat. No. 6,576,019 (2003) a device comprising a biocompatible synthetic or natural polymeric matrix shaped to conform to at least a part of the luminal organ or tissue structure with a first cell population on or in a first area and a second cell population such as a smooth muscle cell population in a second area of the polymeric matrix. The method involves grafting the device to an area in a patient in need of treatment. The polymeric matrix comprises a biocompatible and biodegradable material.

In a second disclosure pertinent to the instant invention on artificial dura mater, Yamauchi et al. [U.S. Pat. No. 7,041,713 (2006)] provided a useful background to the subject of this invention, excerpts of which are summarized below with necessary editing to facilitate readability.

The dura mater is located between the cranium and the brain and around the spinal cord. It principally protects the brain and spinal cord and prevents cerebrospinal fluid leakage. Defects or contractures of the dura mater need to be compensated for and lyophilized human dura mater has been used for that purpose. However, human dura mater has drawbacks such as low homogeneity and limited supply. Further, possible transmission of Creutzfeldt-Jakob disease through the use of human dura mater has been reported. To solve the above noted problems, an artificial dura mater made of silicone was developed. However, silicone dura mater has fallen into disuse as it was reported that silicone dura mater creates a predisposition to meningorrhagia by remaining permanently in vivo because it is non-biodegradable, chronically stimulating the surrounding tissue and causing hypertrophy of the granulation tissue. In contrast, artificial dura maters made of biodegradable and bioabsorbable materials such as collagen were produced but they are not in practical use because of strength-related problems, i.e., because their suture strength is insufficient to allow them to be sutured integrally with the dura mater.

This led Yamauchi et al [U.S. Pat. No. 7,041,713 (2006)] to conceive an artificial dura mater, which comprises an amorphous or low crystallinity polymer as a constituent component and which prevents the cerebrospinal fluid leakage. More specifically, these inventors described a method for preparing an artificial dura mater which is formed as an integral molding of an amorphous or low crystallinity polymer and a structural reinforcement wherein the amorphous or low crystallinity polymer and the structural reinforcement are integrated by bonding, fusion or impregnation, the amorphous or low crystallinity polymer having (1) a degree of crystallinity of 20 percent or lower; (2) an elastic modulus at 4 percent extension of 10 MPa or lower; (3) a $T_g$ of 15° C. or lower; (4) a tensile elongation at break of 200 percent or greater; (5) an elastic modulus at 37° C. of $1 \times 10^8$ Pa or less; and (6) a ratio of relaxation elastic modulus at 23° C./elastic modulus at 37° C. of 0.3 or greater. Meanwhile, the structural reinforcement was described as having (1) an elastic modulus at 5 percent extension of greater than 10 MPa; (2) a $T_g$ of higher than 15° C.; and (3) a tensile elongation at break of less than 200 percent. Furthermore, the amorphous or low crystallinity polymer was noted as having a weight of 10 to 98 percent of the total weight of the integral molding, and the structural reinforcement having a weight of 2 percent or more of the total weight of the integral molding. The method of preparing said artificial dura comprises the step of integrating the amorphous or low crystallinity polymer and the structural reinforcement by bonding, fusing or impregnating to give an integrally molded artificial dura mater.

In a disclosure of general pertinence to the present invention on pelvic floor construction, Tripp et al. [U.S. Pat. No. 6,197,036 (2001)], provided a background to their invention, excerpts of which appear below.

Damage to the pelvic floor is a serious medical condition which may occur during delivery or due to injury to the vesicovaginal fascia. Such an injury can result in a herniation of the bladder called a cystocele. Other similar conditions are known as rectoceles, enteroceles, and enterocystoceles. A rectocele is a herniation of the rectum. An enterocele is formed when the intestine protrudes through a defect in the rectovaginal or vesicovaginal pouch and an enterocystocele is a double hernia in which both the bladder and the intestine protrude. These herniations are serious medical problems that can severely and negatively impact a patient both physiologically and psychologically. Treatment of these conditions requires repositioning of the protruding organs or portions thereof. Existing tissue is often compromised facilitating the need to use a synthetic patch. Current medical procedures for repositioning the protruding organs or portions thereof may be time consuming or invasive. Hence, there is a need for reducing the amount of time which these procedures require and the invasiveness of the procedures. Accordingly, Tripp et al (U.S. Pat. No. 6,197,036 (2001)) disclosed that herniation, including cystocele, rectocele, and enterocystocele may be treated with prefabricated repair patches. The repair patches include a natural or synthetic biocompatible material having a shape adapted to support herniated tissue. The patch also contains a plurality of apertures positioned in the central plane of the patch which may permit ingrowth and may also be an attachment site for fixing sutures. The patch may be covered with coating to decrease the possibility of infection, and/or increase biocompatibility. The coating may also include one or more drugs, for example, an antibiotic, an immunosuppressant, and/or an anticoagulant.

In a second disclosure of general pertinence to the present invention on the use of reinforced foam implants with enhanced integrity for soft tissue repair and regeneration, Binette et al. [U.S. Pat. No. 6,884,428 (2005)] described a biocompatible tissue repair stimulating implant or "scaffold" device that is used to repair tissue injuries, particularly injuries to ligaments, tendons, and nerves. Such implants are especially useful in methods that involve surgical procedures to repair injuries to ligament, tendon, and nerve tissue in the hand and foot. The repair procedures may be conducted with implants that contain a biological component that assists in healing or tissue repair.

Reviewing the above noted disclosures of the prior art show clearly the absence of any absorbable permeability-modulated barrier composites and their use as novel prosthetic devices or for the prevention of adhesion formation. This provided an incentive to explore the new features associated with the instant invention.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

This invention deals with an absorbable, permeability-modulated barrier composite of at least two physicochemically distinct components, wherein one of the components is a flexible film having a thickness of less than about 500. In a preferred embodiment, the flexible film has a thickness of less than about 200 microns and is adjoined directly to an electrostatically spun, non-woven microfibrous fabric, wherein the flexible film is made of (1) a polyaxial copolyester derived from at least two monomers selected from the group consisting of glycolide, l-lactide, ε-caprolactone, trimethylene carbonate, p-dioxanone, 1,5-dioxepan-2-one, and a morpholinedione, (2) a polyether-ester derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione, or (3) a polyether-ester-urethane derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione—the resulting chains of the polyether-ester-glycol are interconnected by urethane linkages formed through the reaction of said polyether-ester-glycol with an aliphatic diisocyanate. The electrostatically spun, non-woven fabric is made of a polyaxial copolyester derived from at least two monomers selected from the group consisting of glycolide, l-lactide, ε-caprolactone, trimethylene carbonate, p-dioxanone, 1,5-dioxepan-2-one, and a morpholinedione. Alternatively, the electrostatically spun, non-woven fabric is made of a polyether-ester derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione.

From a clinical perspective, the instant invention deals with an absorbable, permeability-modulated barrier composite for application as a dura mater prosthesis for use in spinal and cranial surgical procedures as well as for applications dealing with preventing adhesion formation following abdominal and urinogenital surgical procedures.

A specific aspect of this invention deals with an absorbable, permeability-modulated barrier composite of at least two physicochemically distinct components, wherein one component is a flexible film having a thickness of less than about 400 microns, which is adjoined directly to a knitted mesh and indirectly to an electrostatically spun, non-woven microfibrous fabric, wherein the flexible film is made of a (1) polyaxial copolyester derived from at least two monomers selected from the group consisting of glycolide, l-lactide, ε-caprolactone, trimethylene carbonate, p-dioxanone, 1,5-dioxepan-2-one, and a morpholinedione, (2) polyether-ester derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione, or (3) polyether-ester-urethane derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione-the resulting chains of the polyether-ester-glycol are interconnected by urethane linkages formed through the reaction of said polyether-ester-glycol with an aliphatic diisocyanate. The electrostatically spun, non-woven fabric is made of a polyaxial copolyester derived from at least two monomers selected from the group consisting of glycolide, l-lactide, ε-caprolactone, trimethylene carbonate, p-dioxanone, 1,5-dioxepan-2-one, and a morpholinedione. Alternatively, the electrostatically spun, non-woven fabric is made of a polyether-ester derived from a polyether-glycol grafted with at least one monomer selected from the group consisting of glycolide, l-lactide, ε-caprolactone, trimethylene carbonate, p-dioxanone, 1,5-dioxepan-2-one, and a morpholinedione.

A special aspect of this invention deals with an absorbable, permeability-modulated barrier composite of at least two physicochemically distinct components, wherein one component is a flexible film having a thickness of less than about 400 microns, which is adjoined directly to a knitted mesh and indirectly to an electrostatically spun, non-woven microfibrous fabric, wherein the knitted mesh is of a warp-knitted construction and is made of a polyaxial copolyester derived from at least two monomers selected from the group consisting of glycolide, l-lactide, ε-caprolactone, trimethylene carbonate, p-dioxanone, 1,5-dioxepan-2-one, and a morpholinedione. Alternatively, the knitted mesh is of a warp-knitted construction and is made of a polyether-ester derived from a polyether-glycol grafted with one monomer selected from the group consisting of glycolide, l-lactide, ε-caprolactone, trimethylene carbonate, p-dioxanone, 1,5-dioxepan-2-one, and a morpholinedione.

A key clinical aspect of this invention deals with an absorbable, permeability-modulated barrier composite of at least two physicochemically distinct components, wherein one component is a flexible film having a thickness of less than about 400 microns, which is adjoined directly to a knitted mesh and indirectly to an electrostatically spun, non-woven microfibrous fabric, wherein said composite is constructed to be used as a patch for repairing or replacing part of the urinary bladder of a vertebrate animal and/or as a vascular patch for repairing or replacing part of a blood vessel of a vertebrate animal.

Another special aspect of this invention deals with an absorbable, permeability-modulated barrier composite of at least two physicochemically distinct components, wherein one component is a flexible film having a thickness of less than about 500 microns, wherein at least one of its components comprises at least one bioactive agent selected from the group consisting of antimicrobial agents, anesthetic agents, anti-inflammatory agents, and tissue growth-promoting agents.

An important aspect of the instant invention deals with an absorbable, permeability-modulated barrier composite of at least two physicochemically distinct components, wherein one component is a flexible film having a thickness of less than about 500 microns, wherein at least one of its components comprises a hydroswellable polymer, and wherein at least one of its components comprises at least one bioactive agent selected from the group consisting of antimicrobial agents, anesthetic agents, anti-inflammatory agents, and tissue growth-promoting agents.

The present invention generally is directed to absorbable barrier composite constructs, with modulated gas and water permeability, made of a flexible film and at least one fibrous or microfibrous adjoining component in the form of knitted multifilament yarn or electrospun microfibrous, non-woven fabric, respectively. Depending on types of polymeric materials used to produce the individual components of the composite and the mode of constructing these components individually or in different combinations to assemble the final form of the composites, they can be used in a variety of applications in conjunction with several types of surgical procedures. These can be associated with repair, replacement or tissue engineering of components of the digestive tract, respiratory system, neurological tissues, bone, cartilage, urinary tract, genital tract, vascular system and skin. More specific applications entail the use of the composites in plastic surgery, repairing hernial defects at different body sites, and preventing or minimizing adhesion formation following several types of surgical procedures.

Towards constructing barrier composites having a wide range of properties and applicability, chemical structure is one of the basic variables that can be controlled to modulate the properties of the different components of the composites. Accordingly, the polymeric materials can be (1) made of absorbable chains having variable hydrolytic stability by virtue of the type of ester linkages present in the macromolecular chain; (2) made of absorbable polyether-ester-urethane having a range absorption profile, mechanical compliance and hydroswellability-the hydroswellability allows the material to soften and controllably release any bioactive agent therein upon contacting water in the biological environment and to be more compliant and mechanically compatible with different types of soft tissues; and (3) based on copolymeric chains wherein the constituent repeat units are present in a random fashion or segmented and block arrangements. The mode of conversion of the different polymers to the desirable forms is another basic variable that can be controlled to modulate the physico-mechanical properties of the individual components and their performance in the final composite construct. These variables entail those related to (1) fiber formation and fiber processing to knitted mesh; (2) electrospinning, and method of adjoining the microfibrous fabric to other construct components; and (3) film formation and method for adjoining to other construct components.

This invention also deals with controlling the variables discussed above to allow the use of the barrier composites in different applications associated with several types of surgical procedures. Some of the useful applications of the barrier composites of the instant invention entail (1) the use of a bicomponent or tricomponent composite comprising a flexible film adjoined to a microfibrous non-woven fabric or a film adjoined directly to a knitted mesh that is, in turn, adjoined to a microfibrous, non-woven fabric, respectively, as dura substitutes wherein the film prevents leakage, the microfibrous fabric is to accelerate tissue ingrowth and mechanical anchoring, and, if so needed, the knitted mesh provides needed mechanical strength—these are expected to provide immediate restitution of a membranous covering for the brain without inducing any adverse reaction in the host or provoking adhesion to underlying nervous tissue and ideally to absorb and be replaced by tissues similar to the dura mater; (2) the use of a three-component composite as in item 1 in laparoscopic paraesophageal, hernia, and anterior vaginal wall repairs; (3) the use of a two- or three-component composite as in item 1 in spinal surgery repair, wherein at least one of the components is hydroswellable—the use of a synthetic dura prosthesis made of a barrier composite that softens in the biological environment, prevents leakage of the cerebrospinal fluid and post-surgical complications, which increase the patient risk to meningitis and arachnoiditis; and (4) the use of the three-component barrier composite described in item 1 as a patch for repairing or tissue engineering specific sites in the gastrointestinal tract, blood vessels, urinogenital tract, and especially the urinary bladder.

Additional illustrations of this invention are provided in the following examples.

EXAMPLE 1

Synthesis and Characterization of a Typical Film-Forming, Absorbable, Polvaxial, Segmented Copolyester of Glycolide, Trimethylene Carbonate, and F-Caprolactone, P1

The first step for preparing P1 entailed the preparation of a polytrimethylene carbonate polymeric initiator (PPI-1). This was prepared by the ring-opening polymerization of trimethylene carbonate (TMC, 16 g, 0.157 mole) in the presence of trimethylolpropane (TMP) as the initiator at a monomer/initiator ratio of 15 and stannous octanoate (SnOct) as the catalyst at a monomer/catalyst ratio of 10,000. The polymerization was conducted under dry nitrogen in a predried resin kettle equipped for mechanical stirring. The polymerization of TMC was achieved by heating the reaction mixture at 160° C. and keeping it at that temperature until an essentially complete monomer conversion was realized (as determined by GPC); this took about 1.5 hours. In the second step towards preparing P1, the PPI-1 was mixed in the same reaction vessel with glycolide (551.7 g, 4.7556 moles) and ε-caprolactone (232.3 g, 2.038 moles). The reaction mixture was heated to 95° C. to melt the glycolide. The liquid reaction mixture was stirred for 15 minutes at 95° C. prior to adding additional amounts of catalyst to achieve an overall monomer/catalyst ratio of about 32634. The reaction temperature was raised to 180° C. and the polymerization was continued at this temperature for 7 hours; the stirring was maintained until the product became too viscous to stir. At the conclusion of the polymerization, the product was cooled, isolated, and ground. The ground polymer was dried and residual monomer was removed by distillation under reduced pressure. The purified polymer was characterized for molecular weight in terms of inherent viscosity (I.V.) in hexafluoroisopropyl alcohol (HFIP), and thermal properties by differential scanning calorimetry (DSC) and was shown to have an I.V. in HFIP=1.4 dL/g, and a major melting temperature $(T_m)$=215° C.

EXAMPLE 2

Synthesis and Characterization of a Typical Film-Forming, Absorbable Segmented Polyether-Ester of Polyethylene Glycol Linked to a High-Glycolide Copolymeric Segment, P2

A polymerization reactor similar to that described in Example 1 was used to prepare P2 by reacting predried polyethylene glycol having a molecular weight of 20 kDa (PEG-20K, 48 g, 0.0024 mole) with a mixture of glycolide (698.5 g, 6.0223 mole) and trimethylene carbonate (53.41 g., 0.523 mole) in the presence of stannous octanoate as catalyst at a molar monomer/catalyst ratio of $14 \times 10^3$. The polymerization scheme entailed first transferring the PEG-20K into the reactor and heating it under reduced pressure at 140° C. for about 30 minutes. The PEG-20K was then cooled to 95° C. and a mixture of the monomers and catalyst was added and stirred until a liquid mixture was obtained. The reaction temperature was raised to 180° C. and polymerization was continued at this temperature. Stirring of the polymerizing system was maintained until the product became too viscous to stir, and the reaction was then continued for 6 hours. At the conclusion of the polymerization, the product was isolated, purified, and characterized as discussed in Example 1. The purified polymer was shown to have an I.V. in HFIP=1.5 dL/g and $T_m$=223° C.

EXAMPLE 3

Synthesis and Characterization of a Typical Microfiber-Forming, Absorbable Polyaxial, High-Lactide, Segmented Copolyester, P3

Following a similar procedure to that described in U.S. Pat. No. 6,462,169, a triaxial polymeric initiator was made using 35/14/17 (molar) ε-caprolactone (CL)/trimethylene carbonate (TMC)/glycolide (G) and then end-grafted with 34/8 (molar) l-lactide (L)/glycolide. Accordingly, the polymeric initiator was prepared by the ring-opening polymerization of CL (227.3 g, 1.9941 mole), TMC (81.4 g, 0.7977 mole), and G (59.5 g, 0.5128 mole) in the presence of triethanolamine (1.0559 g, $7.0865 \times 10^{-3}$ mole) and stannous octanoate (41.1 mg, $1.0211 \times 10^{-4}$ mole) as the initiator and catalyst, respectively. The polymerization was achieved by heating at 180° C. for 3 hours. The resulting polymeric initiator was cooled to 150° C. and then mixed under nitrogen with l-lactide (279.0 g, 1.9372 mole) and glycolide (52.9 g, 0.4558 mole) and an additional amount of stannous octanoate (41.1 mg, $1.0211 \times 10^{-4}$ mole). The system was stirred while heating to 190-200° C. to achieve a uniform melt. The temperature was then lowered to 140° C. and the reaction was continued without stirring for 24 hours. The polymer was isolated, ground, dried, and heated under reduced pressure to remove unreacted monomer. The polymer was characterized by IR and NMR (for identity), thermal transition ($T_m$=109° C.), and I.V. in chloroform (I.V.=1.4 dL/g).

EXAMPLE 4

Synthesis and Characterization of a Typical Microfiber-Forming, Absorbable, Segmented Polyether-Ester of Polyethylene-Glycol Linked to High-Lactide Copolymeric Segments, P4

Predried crystalline, high molecular weight PEG ($M_w$=12 kDa, 30 g, 0.0025 mole) was mixed, under nitrogen in a stainless steel reactor equipped for mechanical stirring, with a mixture of l-lactide (604.2 g, 4.1958 mole) and TMC (17.8 g, 0.1743 mole) in the presence of stannous octanoate (1.9 g, 0.0163 mole) as a catalyst. The mixture was then heated to achieve complete dissolution of all reactants. The mixing was continued while heating to a polymerization temperature of 140° C. The reaction was maintained at that temperature while stirring until the product became too viscous to stir and essentially complete monomer conversion was achieved (60 hours). At this stage, the reaction was discontinued, the product was cooled, isolated, ground, dried, and traces of residual monomer were removed by distillation under reduced pressure. The purified polymer was characterized from molecular weight (by GPC), I.V., and thermal transition (by DSC) and shown to have a $M_n$=110 kDa, I.V.=1.8 dL/g, and $T_m$=180° C.

EXAMPLE 5

Synthesis and Characterization of a Typical Fiber-Forming, Segmented Polyaxial, High-Glycolide Copolyester, P5

The segmented copolymer P5 was prepared and purified following the method used in preparing P1 using the same polymeric initiator as described in Example 1 with the exception of (1) the amount of polymeric initiator and the components for the second step as shown below, and (2) conducting the second step polymerization, initially, at 180° C. until the polymer melt was too viscous to stir. Then the stirring was discontinued and polymerization continued in the solid state at 180° C. for 5 hours.

Polymeric initiator=16.0 g
Glycolide=745.4 g (6.4262 mole)
ε-Caprolactone=38.6 g (0.3382 mole)
Stannous octanoate=0.966 ml of 0.2 M solution in toluene (1.933×10$^{-4}$ mole) The purified polymer was characterized for its molecular weight in terms of I.V. in HFIP and $T_m$ by DSC, and exhibited an I.V.=1.3 dL/g and $T_m$=220° C.

EXAMPLE 6

Synthesis and Characterization of a Typical Fiber-Forming, Segmented, High-Lactide Copolyester, P6

Segmented l-lactide copolyester (P6) was prepared in two steps, purified, and characterized as generally described in U.S. Pat. No. 6,342,065 (2002). Briefly, in the first step, a polytrimethylene carbonate was made as a polymeric initiator by the ring-polymerization of TMC (58.7 g, 0.575 mole) in the presence of 1,3-propane diol as the initiator and stannous octanoate as the catalyst at a monomer/initiator and monomer/catalyst ratios of 150 and 7000, respectively. The polymerization was conducted by heating at 165° C. until an essentially complete monomer conversion was realized as determined by GPC (about 2 hours). In the second step, the polymeric initiator was cooled to 140° C. and l-lactide (914.3 g, 6.349 mole) and TMC (27.0 g, 0.265 mole) were added, mixed by stirring at that temperature until complete melting of the solid. The reaction mixture was lowered to 110° C. and an additional amount of stannous octanoate (2.585 mL of 0.2 M solution in toluene). The reaction temperature was then raised to 140° C. The polymerization was allowed to continue while stirring until the polymer melt became too viscous to stir. The stirring was then stopped and polymerization was continued for 60 hours at 140° C. At the conclusion of the polymerization, the polymer was isolated, ground, dried, and then purified by distilling the residual monomer by heating at about 100° C. under reduced pressure. The purified polymer was characterized by its I.V. using chloroform as a solvent and Tm using DSC. The polymer exhibited an I.V.=2.8 dL/g and $T_m$=180° C.

EXAMPLE 7

General Method for Preparation of Films, F1 and F2 Using P1 and P2

A 30-ton Carver Laboratory Press (Model 3895-4 PR1A00) with heated platen is used to convert P1 into thin films. The molding process entails placing the ground polymer between two stainless steel plates and heating under pressure at a temperature that is at least 5 degrees above the polymer melting temperature. The pressure, molding time, and cooling scheme are adjusted to provide the proper film thickness.

EXAMPLE 8

General Method for Preparation of Multifilament Yarn and Conversion to Wary-Knitted Mesh M1 and M2

Conversion of P5 and P6 (from Examples 5 and 6) to multifilament yarns, MF5 and MF6, respectively, was pursued as per the melt-spinning protocol described in U.S. Pat. No. 6,342,065 (2002) using specifically a 43-hole die to produce these multifilaments. The extruded multifilaments were further oriented using a one-stage drawing over a heated Godet at about 100-120° C. prior to their use for knitted mesh construction. Processing MF5 and MF6 to produce warp-knitted meshes, M1 and M2, respectively, entailed warping the yarns onto two beams and constructing the meshes using a Raschel Knitting Machine equipped with 18-gauge needles. The meshes were heat-set (or annealed) at 120° C. for one hour. The resulting meshes were tested for weight/unit area and burst strength.

EXAMPLE 9

General Method for Preparation of a Typical Bicomponent Composite (BC) of a Film and Mesh Conversion of P5 and P6 (from Examples 5 and 6) to multifilament yarns, MF5 and MF6, respectively, was pursued as per the melt-spinning protocol described in U.S. Pat. No. 6,342,065 (2002) using specifically a 43-hole die to produce these multifilaments. The extruded multifilaments were further oriented using a one-stage drawing over a heated Godet at about 100-120° C. prior to their use for knitted mesh construction. Processing MF5 and MF6 to produce warp-knitted meshes, M1 and M2, respectively, entailed warping the yarns onto two beams and constructing the meshes using a Raschel Knitting Machine equipped with 18-gauge needles. The meshes were heat-set (or annealed) at 120° C. for one hour. The resulting meshes were tested for weight/unit area and burst strength.

EXAMPLE 10

General Method for Preparation of a Typical Tricomponent Composite (TC) of a Film, Mesh, and Microfibrous Fabric The preparation of a typical tricomponent composite (TC) entails the electrostatic spinning of a solution of a typical microfiber-forming polymer (P3 or P4 from Examples 3 or 4) onto a typical bicomponent composite (BC) from Example 8. The electrostatic spinning process is analogous to the one described earlier [U.S. Pat. No. 7,416,559 (2008)] for depositing a microfibrous mantle on a metallic stent.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. An absorbable, permeability-modulated barrier composite comprising, a first component, a component comprising a knitted mesh, and a component comprising an electrostatically spun, non-woven microfibrous fabric;
   wherein the first component comprises a flexible film comprising a synthetic absorbable polymer comprising
   a) a polyaxial copolyester derived from at least two monomers of glycolide, l-lactide, ε-caprolactone, trimethylene carbonate, p-dioxanone, 1,5-dioxepan-2-one or a morpholinedione;
   b) a polyether ester derived from a polyether-glycol that is grafted with at least one monomer of glycolide, lactide, ε-caprolactone, trimethylene carbonate, p-dioxanone, 1,5-dioxepan-2-one or a morpholinedione; or
   c) a polyether-ester-urethane derived from a polyether-glycol that is grafted with at least one monomer of glycolide, lactide, ε-caprolactone, trimethylene carbonate, p-dioxanone, 1,5-dioxepan-2-one or a morpholinedione, to form a polyether ester glycol, where the polyether ester glycol is interconnected by urethane linkages formed through the reaction of said polyether ester glycol with an aliphatic diisocyanate;
   wherein the knitted mesh component comprises
   a) an absorbable block copolymer comprising a block derived only from trimethylene carbonate and terminal segments derived from glycolide; or
   b) a warp-knitted construction comprising a polyaxial copolyester derived from at least two monomers selected from the group consisting of glycolide, l-lactide, ε-caprolactone, trimethylene carbonate, p-dioxanone, 1,5-dioxepan-2-one, and a morpholinedione; and
   wherein the electrostatically spun, non-woven microfibrous fabric component comprises,
   a) a polyaxial copolyester derived from at least two monomers of glycolide, l-lactide, ε-caprolactone, trimethylene carbonate, p-dioxanone, 1,5-dioxepan-2-one, or a morpholinedione; or
   b) a polyether-ester derived from a polyether-glycol grafted with at least one monomer of glycolide, l-lactide, ε-caprolactone, trimethylene carbonate, p-dioxanone, 1,5-dioxepan-2-one, or a morpholinedione;
   wherein the flexible film is adjoined directly to the component comprising the knitted mesh, and the component comprising the knitted mesh is adjoined directly to the component comprising the electrostatically spun, non-woven microfibrous fabric, to form a layered composite;
   and optionally, wherein at least one of the components comprises a hydroswellable polymer.

2. The absorbable, permeability-modulated barrier composite as in claim 1, wherein at least one of the components comprises at least one bioactive agent, wherein the at least one bioactive agent comprises antimicrobial agents, anesthetic agents, anti-inflammatory agents, or tissue growth-promoting agents.

3. The absorbable, permeability-modulated barrier composite as in claim 1, wherein the flexible film has a thickness of less than 500 microns.

4. The absorbable, permeability-modulated barrier composite as in claim 1, wherein the flexible film has a thickness of less than 200 microns.

5. The absorbable, permeability-modulated barrier composite as in claim 1, wherein
   the flexible film comprises a polyaxial copolyester derived from at least two monomers of glycolide, l-lactide, ε-caprolactone, trimethylene carbonate, p-dioxanone, 1,5-dioxepan-2-one or a morpholinedione;
   and at least one of the following:
   a) the knitted mesh comprises a warp-knitted construction comprising a polyaxial copolyester derived from at least two monomers selected from the group consisting of glycolide, l-lactide, ε-caprolactone, trimethylene carbonate, p-dioxanone, 1,5-dioxepan-2-one, and a morpholinedione;
   b) the microfibrous fabric comprises a polyether-ester derived from a polyether-glycol grafted with derived from at least one monomer of glycolide, l-lactide, ε-caprolactone, trimethylene carbonate, p-dioxanone, 1,5-dioxepan-2-one, or a morpholinedione.

6. The absorbable, permeability-modulated barrier composite as in claim 1, wherein at least one of the components further comprises at least one bioactive agent.

7. A method of performing a spinal or cranial procedure in a subject in need thereof, the method comprising implanting an absorbable, permeability-modulated barrier composite of claim 1 as a dura mater prosthesis in the spinal or cranial area of the subject.

8. A method of preventing surgical adhesions in a subject in need thereof, the method comprising implanting an absorbable, permeability-modulated barrier composite of claim 1 in the area of the subject where the surgery was performed.

9. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 1 to a vertebrate animal for repair, replacement or as a component of the digestive tract, respiratory system, neurological tissues, bone, cartilage, urinary tract, genital tract, vascular system and skin.

10. A method for repairing or tissue engineering one or more specific sites in the gastrointestinal tract, blood vessels, urinogenital tract, or urinary bladder of a vertebrate animal, the method comprising applying an absorbable, permeability- modulated barrier composite of claim 1 as a patch to the one or more sites in the gastrointestinal tract, blood vessels, urinogenital tract, or the urinary bladder of the vertebrate animal.

11. A method of performing a spinal or cranial procedure in a subject in need thereof, the method comprising implanting an absorbable, permeability-modulated barrier composite of claim 5 as a dura mater prosthesis in the spinal or cranial area of the subject.

12. A method of preventing surgical adhesions in a subject in need thereof, the method comprising implanting an absorbable, permeability-modulated barrier composite of claim 6 in the area of the subject where surgery was performed.

13. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 6 to a vertebrate animal for repair, replacement or as a component of the digestive tract, respiratory system, neurological tissues, bone, cartilage, urinary tract, genital tract, vascular system and skin.

14. A method for repairing or tissue engineering one or more specific sites in the gastrointestinal tract, blood vessels, urinogenital tract, or urinary bladder of a vertebrate animal, the method comprising applying an absorbable, permeability-modulated barrier composite of claim 6 as a patch to the one or more sites in the gastrointestinal tract, blood vessels, urinogenital tract, or the urinary bladder of the vertebrate animal.

15. A method of performing a surgical procedure or reducing surgical adhesions in a subject in need thereof, the method comprising implanting an absorbable, permeability-modulated barrier composite of claim 7 in the area of the subject where the surgical procedure was performed.

16. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 7 to a vertebrate animal for repair, replacement or as a component of the digestive tract, respiratory system, neurological tissues, bone, cartilage, urinary tract, genital tract, vascular system and skin.

17. A method for repairing or tissue engineering one or more specific sites in the gastrointestinal tract, blood vessels, urinogenital tract, or urinary bladder of a vertebrate animal, the method comprising applying an absorbable, permeability-modulated barrier composite of claim 7 as a patch to the one or more sites in the gastrointestinal tract, blood vessels, urinogenital tract, or the urinary bladder of the vertebrate animal.

18. An absorbable, permeability-modulated barrier composite comprising, a first component, a component comprising a knitted mesh, and a component comprising an electrostatically spun, non-woven microfibrous fabric;

wherein the first component comprises a flexible film comprising a synthetic absorbable polymer comprising
a) a polyaxial copolyester derived from at least two monomers of glycolide, l-lactide, ε-caprolactone, trimethylene carbonate, p-dioxanone, 1,5-dioxepan-2-one or a morpholinedione;
b) a polyether ester derived from a polyether-glycol that is grafted with at least one monomer of glycolide, lactide, ε-caprolactone, trimethylene carbonate, p-dioxanone, 1,5-dioxepan-2-one or a morpholinedione; or
c) a polyether-ester-urethane derived from a polyether-glycol that is grafted with at least one monomer of glycolide, lactide, ε-caprolactone, trimethylene carbonate, p-dioxanone, 1,5-dioxepan-2-one or a morpholinedione, to form a polyether ester glycol, where the polyether ester glycol is interconnected by urethane linkages formed through the reaction of said polyether ester glycol with an aliphatic diisocyanate;

wherein the knitted mesh component comprises
a) an absorbable block copolymer comprising a block derived only from trimethylene carbonate and terminal segments derived from glycolide; or
b) a warp-knitted construction comprising a polyaxial copolyester derived from at least two monomers selected from the group consisting of glycolide, l-lactide, ε-caprolactone, trimethylene carbonate, p-dioxanone, 1,5-dioxepan-2-one, and a morpholinedione; and wherein the electrostatically spun, non-woven microfibrous fabric component comprises,
a) a polyaxial copolyester derived from at least two monomers of glycolide, l-lactide, ε-caprolactone, trimethylene carbonate, p-dioxanone, 1,5-dioxepan-2-one, or a morpholinedione; or
b) a polyether-ester derived from a polyether-glycol grafted with at least one monomer of glycolide, l-lactide, ε-caprolactone, trimethylene carbonate, p-dioxanone, 1,5-dioxepan-2-one, or a morpholinedione;

wherein the flexible film is adjoined directly to the knitted mesh and the microfibrous fabric is adjoined directly to the knitted mesh, such that the flexible film and the microfibrous fabric are indirectly joined to each other with the knitted mesh sandwiched there between;
and optionally, wherein at least one of the components comprises a hydroswellable polymer.

19. The absorbable, permeability-modulated barrier composite as in claim 18, wherein at least one of the components comprises at least one bioactive agent, wherein the at least one bioactive agent comprises antimicrobial agents, anesthetic agents, anti-inflammatory agents, or tissue growth-promoting agents.

20. The absorbable, permeability-modulated barrier composite as in claim 18, wherein the flexible film has a thickness of less than 500 microns.

21. The absorbable, permeability-modulated barrier composite as in claim 18, wherein the flexible film has a thickness of less than 200 microns.

22. The absorbable, permeability-modulated barrier composite as in claim 18, wherein
the flexible film comprises a polyaxial copolyester derived from at least two monomers of glycolide, l-lactide, ε-caprolactone, trimethylene carbonate, p-dioxanone, 1,5-dioxepan-2-one or a morpholinedione; and at least one of the following:
a) the knitted mesh comprises a warp-knitted construction comprising a polyaxial copolyester derived from at least two monomers selected from the group consisting of glycolide, l-lactide, ε-caprolactone, trimethylene carbonate, p-dioxanone, 1,5-dioxepan-2-one, and a morpholinedione;

b) the microfibrous fabric comprises a polyether-ester derived from a polyether-glycol grafted with derived from at least one monomer of glycolide, l-lactide, ε-caprolactone, trimethylene carbonate, p-dioxanone, 1,5-dioxepan-2-one, or a morpholinedione.

23. The absorbable, permeability-modulated barrier composite as in claim 18, wherein at least one of the components further comprises at least one bioactive agent.

24. A method of performing a spinal or cranial procedure in a subject in need thereof, the method comprising implanting an absorbable, permeability-modulated barrier composite of claim 18 as a dura mater prosthesis in the spinal or cranial area of the subject.

25. A method of preventing surgical adhesions in a subject in need thereof, the method comprising implanting an absorbable, permeability-modulated barrier composite of claim 18 in the area of the subject where the surgery was performed.

26. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 18 to a vertebrate animal for repair, replacement or as a component of the digestive tract, respiratory system, neurological tissues, bone, cartilage, urinary tract, genital tract, vascular system and skin.

27. A method for repairing or tissue engineering one or more specific sites in the gastrointestinal tract, blood vessels, urinogenital tract, or urinary bladder of a vertebrate animal, the method comprising applying an absorbable, permeability-modulated barrier composite of claim 18 as a patch to the one or more sites in the gastrointestinal tract, blood vessels, urinogenital tract, or the urinary bladder of the vertebrate animal.

28. A method of performing a spinal or cranial procedure in a subject in need thereof, the method comprising implanting an absorbable, permeability-modulated barrier composite of claim 22 as a dura mater prosthesis in the spinal or cranial area of the subject.

29. A method of preventing surgical adhesions in a subject in need thereof, the method comprising implanting an absorbable, permeability-modulated barrier composite of claim 23 in the area of the subject where surgery was performed.

30. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 23 to a vertebrate animal for repair, replacement or as a component of the digestive tract, respiratory system, neurological tissues, bone, cartilage, urinary tract, genital tract, vascular system and skin.

31. A method for repairing or tissue engineering one or more specific sites in the gastrointestinal tract, blood vessels, urinogenital tract, or urinary bladder of a vertebrate animal, the method comprising applying an absorbable, permeability-modulated barrier composite of claim 23 as a patch to the one or more sites in the gastrointestinal tract, blood vessels, urinogenital tract, or the urinary bladder of the vertebrate animal.

32. A method of performing a surgical procedure or reducing surgical adhesions in a subject in need thereof, the method comprising implanting an absorbable, permeability-modulated barrier composite of claim 24 in the area of the subject where the surgical procedure was performed.

33. A method for repair, replacement or tissue engineering of components of the digestive tract, respiratory system, neurological tissues, bone, cartilage, urinary tract, genital tract, vascular system and skin of a vertebrate animal, the method comprising providing an absorbable, permeability-modulated barrier composite of claim 24 to a vertebrate animal for repair, replacement or as a component of the digestive tract, respiratory system, neurological tissues, bone, cartilage, urinary tract, genital tract, vascular system and skin.

34. A method for repairing or tissue engineering one or more specific sites in the gastrointestinal tract, blood vessels, urinogenital tract, or urinary bladder of a vertebrate animal, the method comprising applying an absorbable, permeability-modulated barrier composite of claim 24 as a patch to the one or more sites in the gastrointestinal tract, blood vessels, urinogenital tract, or the urinary bladder of the vertebrate animal.

* * * * *